United States Patent [19]

Dale et al.

[11] Patent Number: 4,893,619
[45] Date of Patent: Jan. 16, 1990

[54] HUMERAL OSTEOTOMY GUIDE

[75] Inventors: James L. Dale, Austin; Brian D. Burkinshaw, Pflugerville; Wayne Z. Burkhead, Dallas, all of Tex.

[73] Assignee: Intermedics Orthopedics, Inc., Austin, Tex.

[21] Appl. No.: 152,145

[22] Filed: Feb. 4, 1988

[51] Int. Cl.⁴ .............................................. A61F 5/04
[52] U.S. Cl. ........................................ 606/87; 606/82
[58] Field of Search .......... 128/92 YD, 92 V, 92 VZ, 128/92 YU, 92 VS, 92 VY, 91 A, 92 R, 92 VY, 92 VD; 269/328

[56] References Cited

U.S. PATENT DOCUMENTS

| 4,364,381 | 12/1982 | Sher | 128/92 VD |
| 4,524,766 | 6/1985 | Petersen | 128/92 VW |
| 4,627,425 | 12/1986 | Reese | 128/92 VY |
| 4,757,810 | 7/1988 | Reese | 128/92 VY |

FOREIGN PATENT DOCUMENTS

| 0225374 | 3/1968 | U.S.S.R. | 128/92 VY |
| 1448111 | 9/1976 | United Kingdom | 128/92 VD |
| 2159680 | 12/1985 | United Kingdom | 128/92 VY |

Primary Examiner—Robert A. Hafer
Assistant Examiner—Michael Brown
Attorney, Agent, or Firm—John R. Merkling

[57] ABSTRACT

A device for guiding an osteotomy to be performed on the proximal end of a humerus that has a proximal sawguide alignable on a selected surface of the proximal end of the humerus for defining a saw line thereon; a radial arm connecting the sawguide to a distal mechanism for stably aligning the sawguide, the distal alignment mechanism has a pair of opposing lateral and medial epicondyle arms pivotally engageable with the lateral and medial sides of the distal end of the humerus, the epicondyle arms being pivotally mounted in a distal cross arm, the distal end of the radial arm being slidably mounted in the cross arm for distal to proximal slidable movement therein; the proximal end of the radial arm being rotatably connected to the sawguide through a proximal guide bar; the radial arm being supported above the humerus by the proximal guide bar and the epicondyle arms.

21 Claims, 7 Drawing Sheets

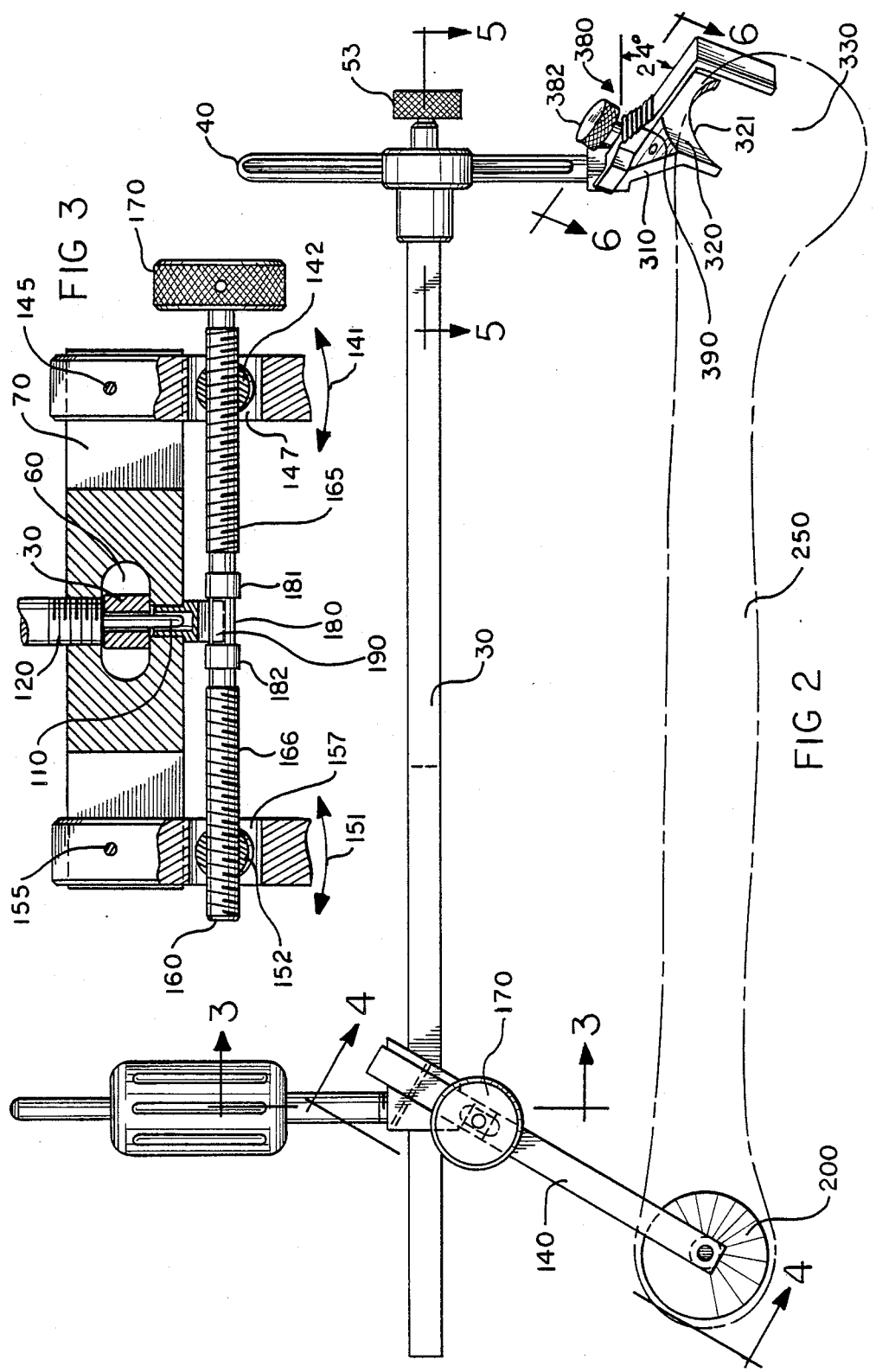

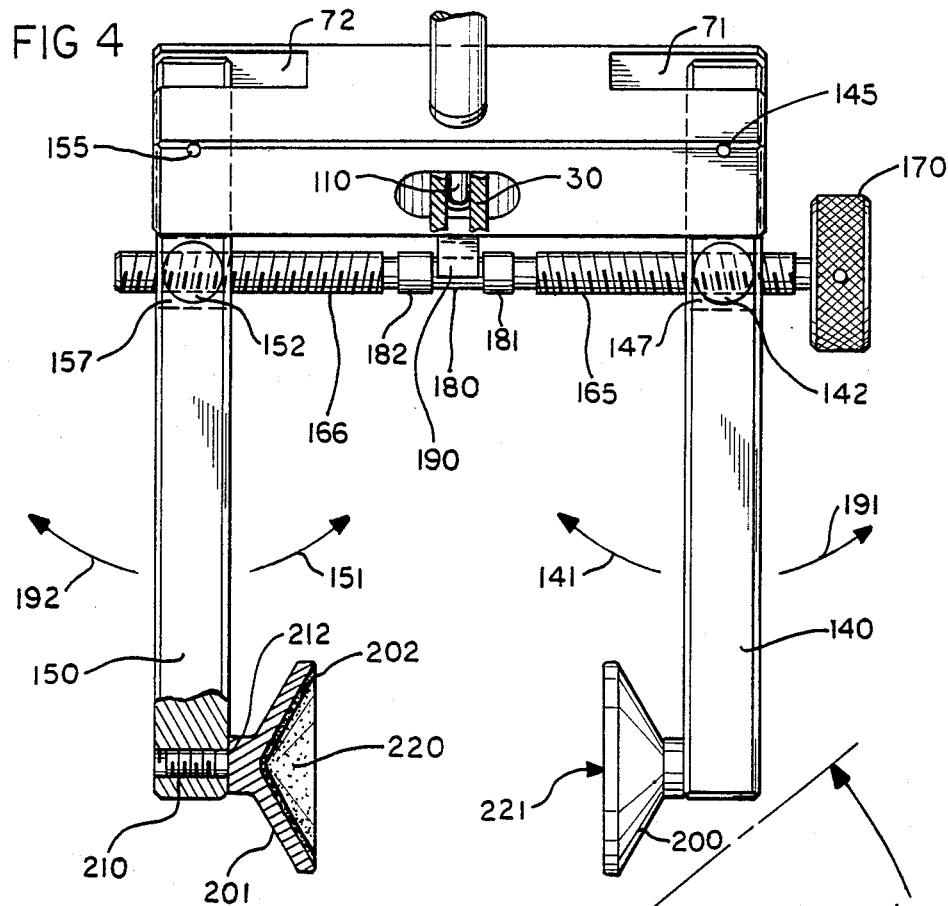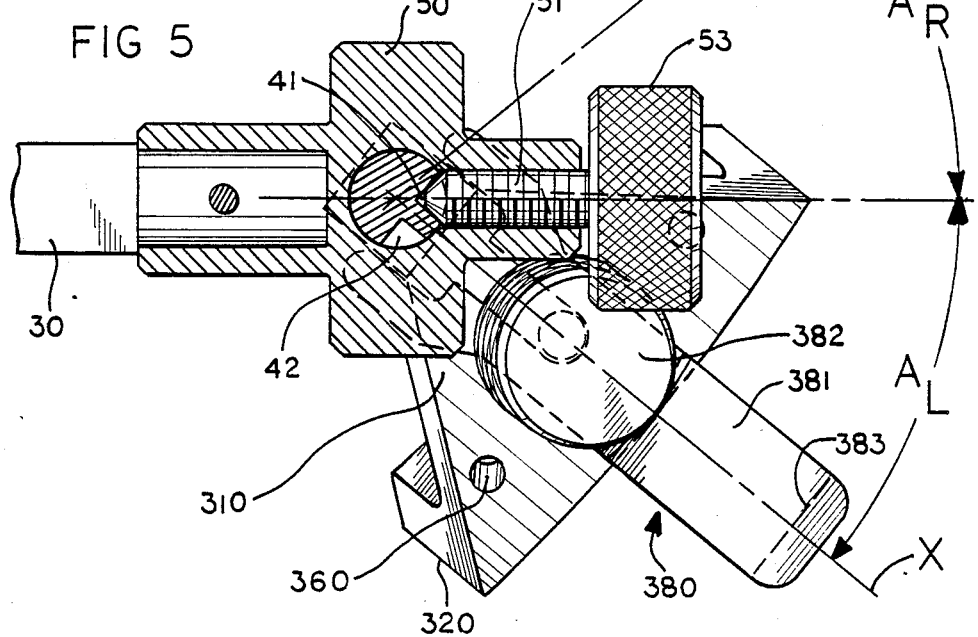

HUMERAL OSTEOTOMY GUIDE

BACKGROUND OF THE INVENTION

The present invention relates to surgical devices for assisting in the implantation of prostheses and more particularly to devices for assisting the surgeon in performing osteotomy or bone cutting in preparation for humeral prosthetic device implantation.

Prosthetic implant devices for use in reconstructing the proximal area of the human humerus are typically designed so as to closely mimic the natural bone anatomy of the proximal end of the humerus. The surgeon who is equipped with such humeral prosthetic devices is thus confronted with the task of performing as precise an osteotomy or bone cutting as possible which will accomodate the size and structure of the prosthetic device to be implanted. Prior techniques for performing an osteotomy to accomodate implantation of a humeral prosthesis have simply involved the careful and painstaking attention of the surgeon by eyesight to determine an appropriate site on the proximal end of the humerus for performance of the osteotomy.

It is an object of the invention therefore to provide a device for assisting the surgeon in the performance of a humeral osteotomy. It is a further object of the invention to provide a device which defines a proximal humeral osteotomy line and which guides the surgeon in the performance of the bone cutting.

SUMMARY OF THE INVENTION

In accordance with the invention there is provided a device for guiding an osteotomy to be performed on the proximal end of a human humerus comprising: a proximal end sawguide for defining an osteotomy saw line on the proximal end of the humerus; a distal end mechanism for stably aligning the sawguide on the proximal end of the humerus; a radial arm connecting the sawguide and the mechanism for aligning; the radial arm being rotatably connected to the sawguide at a proximal end thereof for rotatable movement of the sawguide for use in connection with a left or right humerus; the radial arm being slidably mounted at a distal end in the mechanism for aligning for slidable movement of the radial arm in the distal to proximal direction; the sawguide engaging a selected surface on the proximal end of the humerus and supporting the proximal end of the radial arm above the humerus; the mechanism for aligning engaging the distal end of the humerus and supporting the distal end of the radial arm above the humerus.

The mechanism for aligning typically includes a distal cross arm having a slot therethrough, the distal end of the radial arm being slidably received through the slot such that the radial arm is slidable in the proximal to distal direction, the cross arm including a screw for frictionally locking the radial ar within the slot at selected distal to proximal positions. The screw typically has a pin protruding from its end into the slot and through the radial slot of the radial arm, the radial arm being rotatable around the pin and lockable with the screw in selected rotatable positions.

In alternative embodiments of the invention the radial arm may comprise a telescoping arm fixedly connected proximally to the sawguide and distally to the alignment mechanism. Such a telescoping radial arm is preferably extendable and contractable in length such that the distal to proximal distance between the proximal sawguide and the alignment mechanism may be varied and adjusted by the user to accomodate humeri of varying lengths.

The mechanism for aligning typically includes a pair of opposing epicondyle arms pivotably connected to opposing ends of the distal cross arm, the epicondyle arms including cups for receiving and engaging the distal end of the humerus, the epicondyle arms being pivotable toward and away from each other for allowing the cup to reversibly receive and engage the distal end of the humerus, the distal cross arm having a slot for slidably receiving the radial arm, the radial arm being slidable in the slot in the distal to proximal direction for varying the distal to proximal length between the sawguide and the alignment mechanism.

The mechanism for aligning preferably includes a cross screw connected to both of the epicondyle arms for pivoting the epicondyle arms toward and away from each other around their pivotable connection to the distal cross arm. The cross screw typically has a left hand screw end screwably connected to one of the epicondyle arms and a right hand screw end screwably connected to the other of the epicondyle arms, the cross-screw being turnable in clockwise and counterclockwise directions, the epicondyle arms being pivotable toward each other upon turning of the cross-screw in one of the clockwise or counterclockwise directions and pivotable away from each other upon turning of the cross-screw in the other of the clockwise or counterclockwise directions.

In alternative embodiments, the epicondyle arms may be connected by alternative mechanism such as spring, elastic or similar mechanisms which urge the arms toward each other under a predetermined amount of force sufficient to allow the cup or other distal humeral end receiving mechanisms to snugly engage the distal end of the humerus and thus stabilize and align the device on the humerus. In such embodiments the arms may be manually urged or pivoted away from each other to allow the proximal humeral end receiving mechanisms to be aligned with opposing surfaces on the distal end of the humerus to be received, and then released to allow the arms to pivot toward each other.

The device typically includes followers pivotably mounted in each of the epicondyle arms, the followers having complementary threaded apertures for screwably receiving the right and left hand screw ends of the cross screw and being pivotably mounted in the epicondyle arms such that when the cross screw is turned the epicondye arms pivot within the distal cross arm and the followers simultaneously pivot within the epicondyle arms.

A stabilizer for restricting transverse movement of the cross-screw relative to the distal cross arm is preferably provided, the stabilizer having a transverse aperture for rotatably receiving the cross screw, the crossscrew having a selected length rotatably received within the transverse aperture of the stabilizer and including bosses for engaging a surface of the stabilizer and limiting movement of the cross screw reative to the cross arm.

The device typically includes a proximal guide bar connecting the proximal end of the radial arm and the sawguide, one end of the guide bar being rotatably disposed within a complementary mounting aperture in the proximal end of the radial arm, the other end of the guide bar being fixedly connected to the sawguide, the sawguide being rotatable in the lateral to medial direction by rotation of the guide bar within the mounting aperture. The radial arm preferably includes a screw for frictionally engaging and locking the guide bar in selected rotational positions within the complementary aperture.

The guide bar may be axially slidable within the aperture in the proximal end of the radial arm, the locking screw being engagable with the bar such that the bar may be frictionally engaged and locked in selected axial positions.

The guide bar preferably includes a pair of axial grooves for receiving and engaging the lock screw, the grooves being disposed at selected positions on the surface of the guide bar such that the sawguide is disposed at preselected rotational positions relative to the radial arm when the lock screw is lockably engaged within the grooves.

The sawguide typically comprises a guide plate extending outwardly from the axis of the guide bar, the guide plate having a proximal end guide surface for defining a saw line on the proximal end of the humerus, the underside edge of the guide surface having a contour complementary to the contour of the head of the humerus for receiving and engaging a selected surface on the head of the humerus. The guide plate preferably includes at least two apertures for receiving a pair of stabilizer pins therethrough, the axes of the apertures being disposed at an angle of greater than zero degrees relative to each other.

The device preferably includes a stylus disposed on the anterior surface of the guide plate for measuring the size, e.g. radial head heights, of the proximal end of the humerus which is to be resected and replaced with a proximal humeral prosthetic device whose size may be predetermined on the basis of the measurement made with the stylus. The stylus typically comprises a measuring arm slidable along the anterior surface of the guide plate in the distal to proximal direction, the measuring arm having a slot slidably receiving a screw screwably engaged within a complementary threaded aperture in the guide plate, and frictionally engageable with the anterior surface of the measuring arm along the length of the slot, the measuring arm having a measuring surface extending proximally beyond and facing the end guide surface for engaging the proximal tip of the humerus, the measuring arm being slidable in the distal to proximal direction such that the measuring surface is slidably movable into engagement with the proximal tip of the humerus and lockable in such position by frictionally lockable engagement of the screw along the length of the slot.

BRIEF DESCRIPTION OF THE DRAWINGS

FIG. 2 is a side view of the device of FIG. 1 showing a typical positioning of the device on a human humerus in preparation for performing an osteotomy;

FIG. 3 is a partial sectional view of the distal cross arm section of the device of FIG. 1 taken along lines 3—3 of FIG. 2;

FIG. 4 is a partial sectional view of the distal end of the device of FIG. 1 taken along lines 4—4 of FIG. 2;

FIG. 5 is a partial sectional, anterior view of the proximal end of the device of FIG. 1 taken along lines 5—5 of FIG. 2;

DETAILED DESCRIPTION OF THE INVENTION

Following is a description of an embodiment of the invention.

Figure 1:
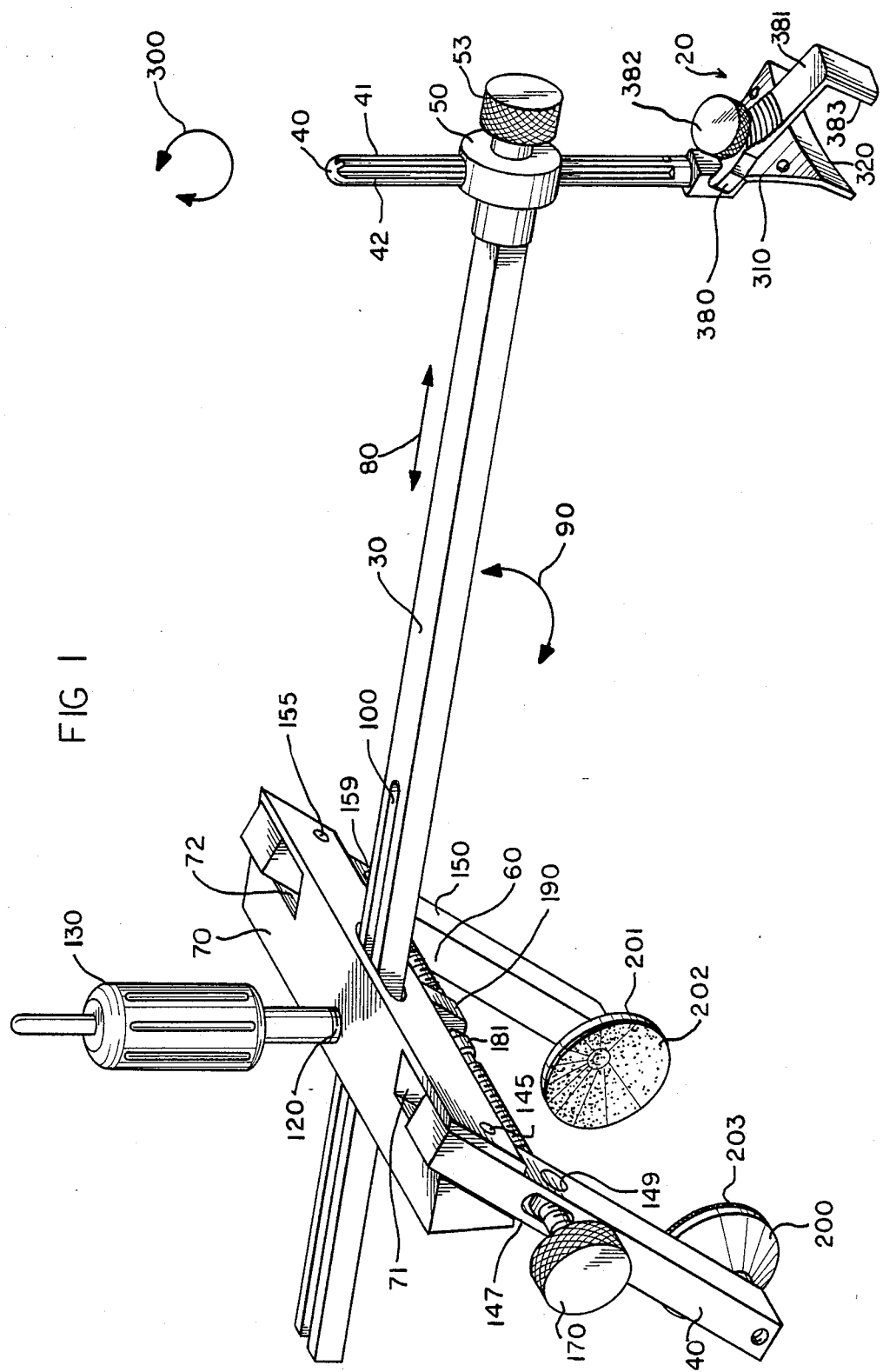
FIG. 1 is a side isometric view of a humeral osteotomy guide device according to the invention.

A humeral osteotomy guide 10 according to the invention is shown in FIG. 1. The device comprises a sawguide 20 which 1s connected to a radial arm 30 by a guide bar 40 which is rotatably received through a complementary aperture in a proximal mounting joint 50 which is fixedly connected to the proximal end of the arm 30.

The distal end of arm 30 is slidably received through a tranverse aperture 60, FIGS. 1, 2 provided in a distal cross arm 70 such that arm 30 may be adjustably moved in the proximal to distal direction 80 relative to the cross arm 70. The arm 30 is preferably provided with a distal radial slot 100, FIG. 1, for slidably and rotatably receiving a pin 110, FIG. 2, which extends from the end surface of a tightening or lock screw 120. The lock screw 120 is engaged in a complementary threaded aperture provided in cross arm 70 and is screwable through the body of arm 70 and into slot 60. When the slot 100 of arm 30 is positioned such that the pin 110 is disposed therein, the pin 110 serves to limit lateral to medial movement of the arm 30 within the slot 100 while at the same time allowing arm 30 to rotate in the direction 90 around pin 110 and further allowing arm 30 to be slid in the distal to proximal direction 80. Arm 30 is lockable into a fixed position relative to arm 70 by appropriately turning knob 130 which is connected to screw 120 thus causing the bottom end surface of screw 120 to engage the top surface of arm 30 which is disposed within slot 60. Sufficient turning of knob 130 will thus eventually cause the bottom end surface of screw 120 to exert enough frictional pressure on the top surface of arm 30 such that arm 30 is frictionally locked in a selected position within slot 60.

A pair of opposing epicondyle arms 140, 150 are pivotably mounted at one of their ends in complementary slots 71, 72 which are provided in the respective ends of arm 70, FIGS. 1, 3, 4. Pivot pins 145, 155 are fixedly inserted by conventional means in arm 70 and extend through arms 140, 150 respectively such that arms 140, 150 may pivot in the lateral to medial directions 141, 191, 151, 192 relative to arm 70 around pins 145, 155. A cross screw 160 having left hand end screw 165 and right hand end screw 166 sections (or vice versa) extends between and screwably connects arms 140, 150. The screw sections 165, 166 are connected to arms 140, 150 by being screwably engaged in complementary threaded apertures provided in a pair of follower pivots 142, 152. The follower pivots comprise generally cylindrical elements 142, 152 rotatably mounted in slots 147, 157 provided in arms 140, 150 and may have axial pins 149, 159 which are rotatably mounted in complementary apertures provided in the body of arms 140, 150 or, the ends of cylindrical elements 142, 152 may simply be rotatably mounted in complementary apertures in the body of arms 140, 150.

The cross screw 160 is provided with a section 180 having a pair of lateral to medial movement stabilizing bosses 181, 182, FIGS. 1, 3, 4 which cooperate with a stabilizer arm 190 to prevent the arms 140, 150 from moving uncontrollably in the lateral to medial direction. As shown in the embodiment of FIGS. 1, 3, 4 the arm 190 is connected to and protrudes downwardly from the underside of cross arm 70, and encircles part or all of the circumference of section 180 of the cross screw 160. Bosses 181, 182 protrude outwardly beyond the circumference of section 180 and the centrally disposed side edges of bosses 181, 182 engage against the side edges of stabilizer arm 190 to prevent the cross screw 160 and the arms 140, 150 to which the cross screw 60 is screwably connected from moving uncontrollably in the lateral to medial direction relative to the cross arm 70. Stabilizer arm 190 is typically formed as an integral protrusion from the underside of arm 70 and bosses 181, 182 are typically formed as integral protrusions from the screw 160.

As shown in FIGS. 1, 2, 4, 8 epicondyle cups 200, 201 are provided on the ends of arms 140, 150 respectively. The cups 200, 201 are typically rotatably connected to the ends of the arms 140, 150 by conventional means such as a screw mechanism 210 having a rotatable pin 212 connector to the cups 201, 200. The cups 200, 201 include cup-shaped receiving apertures such as aperture 220, FIG. 4, which is typically configured so as to be generally complementary with the shape of the internal 230 and external 240 condyles FIG. 8 on the distal end of a human humerus 250, FIGS. 2, 8, 9, 10. The cups 200, 201 may be provided with a layer 203, 202, FIGS. 1, 4, of rubber, plastic, foam, or other material overlying the surface of receiving apertures 220, 221 for purposes of better enabling a snug engagement of receiving apertures 220, 221 with the distal end of the humerus 250 when the arms 140, 150 are appropriately pivoted so as to effect such engagement.

Figure 8:
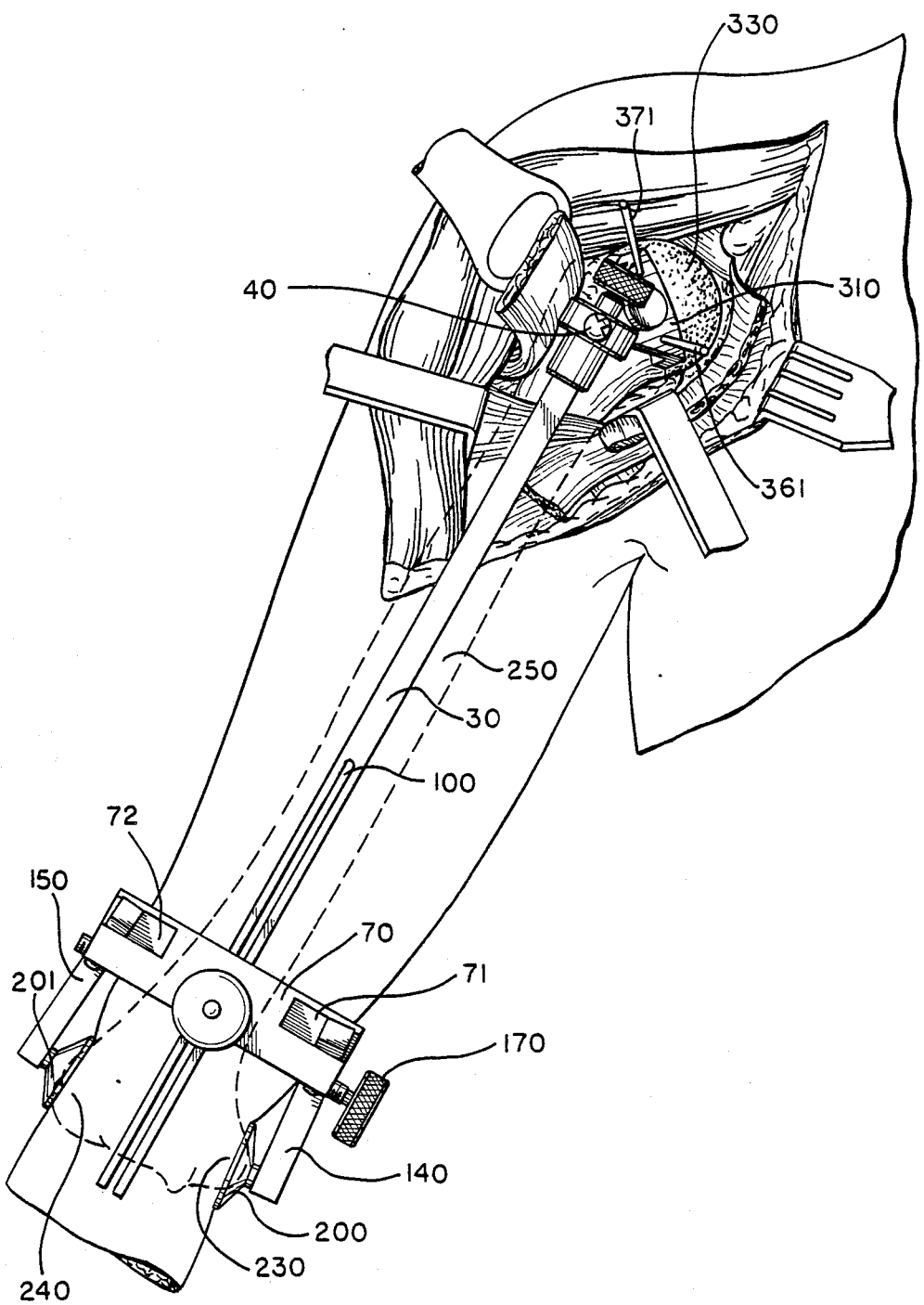
FIG. 8 is an anterior view of the device showing the device as it might typically be positioned on the human arm during the course of proximal humeral area surgery.

In normal use the device 10, is positioned above the humerus, typically above the anterior aspect, and the knob 170 is appropriately turned so as to pivot the arms 140, 150 outwardly 191, 192 such that the distance between the cups 200, 201 is greater than the lateral to medial distance between the condyles 230, 240. The apertures of the cups 200, 201 are aligned with the condyles 230, 240 in the lateral to medial direction and the knob 170 is then appropriately turned so as to cause the arms 140, 150 to pivot inwardly 141, 151 toward each other until the apertures of the cups 200, 201 receive and snugly engage the condyles 230, 240 and any immediately overlying tissue such as skin, muscle, ligaments and the like as shown in FIG. 8. The pivoting movement 141, 191, 151, 192 of the arms 140, 150 occurs as a result of the cross screw sections 165, 166 exerting inward 141, 151 or outward 191, 192 screwing force on the arms 140, 150 by turning engagement of screw sections 165, 166 within the threaded apertures provided in follower pivot cylinders 142, 152 which in turn follow the pivoting of the arms 140, 150 by means of pivot pins 149, 159 which are rotatably mounted in arms 140, 150.

Once the cups 200, 201 are snugly engaged on the condyles 230, 240, FIGS. 2, 8, the radial arm 30 is stably supported above the humerus 250 by virtue of its mounting within slot 60 of arm 70.

As described above the sawguide 20 is fixedly attached to the lower end of guide bar 40, FIGS. 1, 2, 5, 9, which is rotatably received within a cylindrical aperture provided in mounting joint 50 such that the bar 40 may be rotated in the direction of arrows 300, FIG. 1. Most preferably, bar 40 is provided with angle alignment grooves 41, 42 for purposes of lockably receiving and engaging the complementary shaped end of an alignment screw 51, FIG. 5, which is screwably engaged and turnable within a complementary threaded aperture provided in the body of mounting joint 50. By appropriate turning of knob 53 which is connected to the outside end of screw 51, screw 51 may be screwed such that the end of the screw frictionally engages the edges of a groove 41, 42 and locks the bar 40 in a fixed rotational position relative to the axis of radial arm 30. For example, as shown in FIG. 5, the screw 51 is lockably engaged within groove 41 thus fixing bar 40 in a fixed rotational position relative to arm 30. The grooves 41, 42 are disposed on the surface of bar 40 at preselected positions such that when the grooves are lockably engaged with the screw 51, the axis X of the sawguide 20 is disposed at preselected lateral to medial angles relative to the axis of arm 30. As shown in FIG. 5, the grooves are disposed at positions on the surface of bar 40 such that the axis, X, of the sawguide may be locked into a left side, $A_L$, or right side, $A_R$, angle relative to the axis of arm 30. Preferably, the positioning of grooves 41, 42 on the surface of bar 40 relative to the fixed connection of sawguide 20 on the end of bar 40, is preselected such that the axis, X, of the sawguide may be fixed at left or right, $A_L$, $A_R$, angles of between about 25 and about 55 degrees relative to the axis of the arm 30 and most preferably at left or right, $A_L$, $A_R$ angles of about 39 degrees. In alternative embodiments of the invention the bar 40 may be provided with other mechanisms, other than grooves 41, 42 for locking the bar 40 at the predetermined angular positions $A_L$, $A_R$. Such alternative mechanisms might comprise, for example, a pair of apertures drilled in bar 40 whose axes are disposed relative to the fixed attachment of plate 310 such that when screw 51 is received by such apertures, the axis X of sawguide 20 is disposed at the predetermined angles $A_L$, $A_R$ relative to arm 30. Another mechanism such as a transverse slot provided in bar 40 for engagement with screw 51, the slot having terminal surfaces which limit the rotation of bar 40 to the selected degree of angles $A_L$, $Z_R$.

The sawguide assembly 20 comprises a guide plate 310 having an end guide surface 320, FIGS. 1, 2, 5, 6, 7, 8, 9. The bottom edge 321 of the guide surface 320 is typically curvedly contoured so as to receive and complement the surface of the proximal end 330 of a human humerus 250, in particular the head area of the humerus 250. The bottom edge 321 of the end surface 320 is manually positioned and eventually locked into the position shown in FIGS. 7, 8 by adjustably sliding arm 30 to a desired position in the directions 80, 90 and adjustably rotating bar 40 to a desired distal to proximal and angular position and, when edge 321 is finally positioned at a desired location on the proximal humeral end 330 for eventual performance of the osteotomy, FIG. 9, knobs 130 and 53 are tightened so as to lockably engage arm 30 and bar 40 and thus also lockably fix end surface 320 and edge 321 in the desired position.

Figure 6:
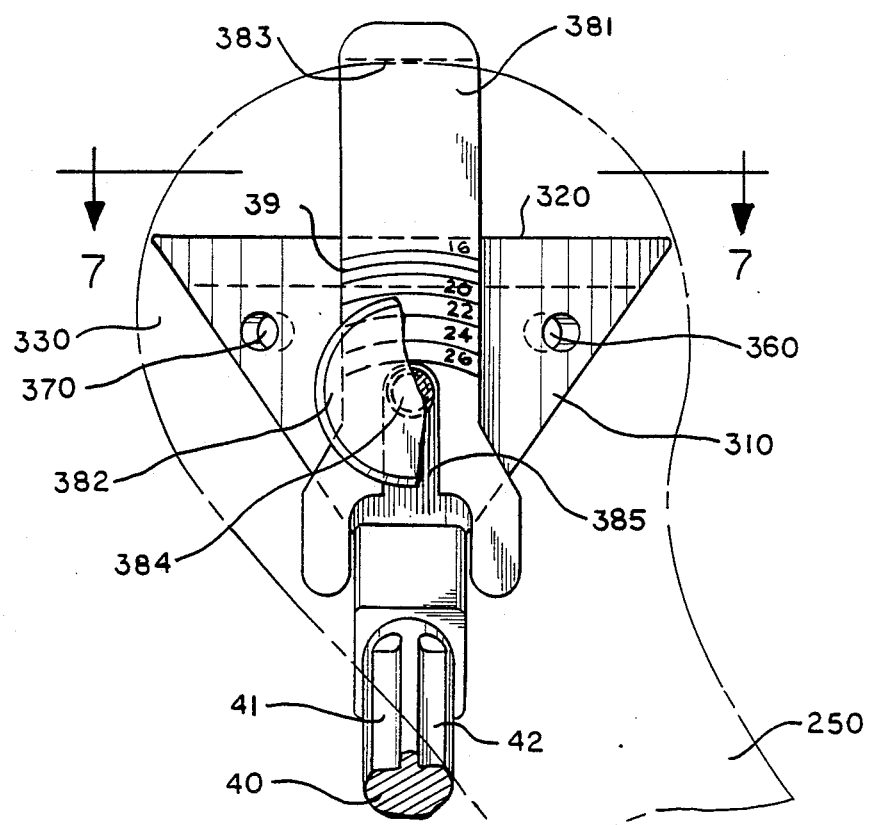
FIG. 6 is a proximal anterior view of the sawguide, stylus and guide bar elements of the device of FIG. 1 taken along lines 6—6 of FIG. 2.
Figure 7:
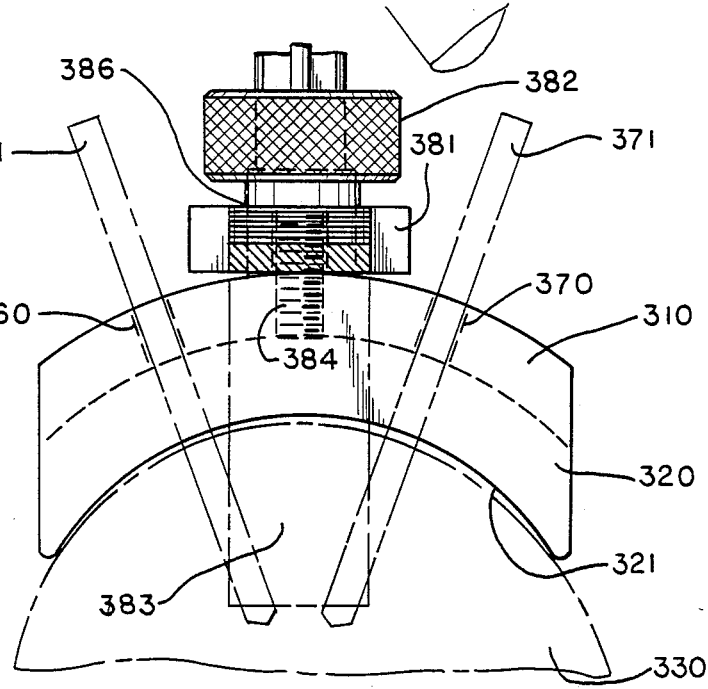
FIG. 7 is an angled proximal view of the sawguide, stylus and guide bar elements of the device of FIG. 1 taken along lines 7—7 of FIG. 6.
Figure 9:
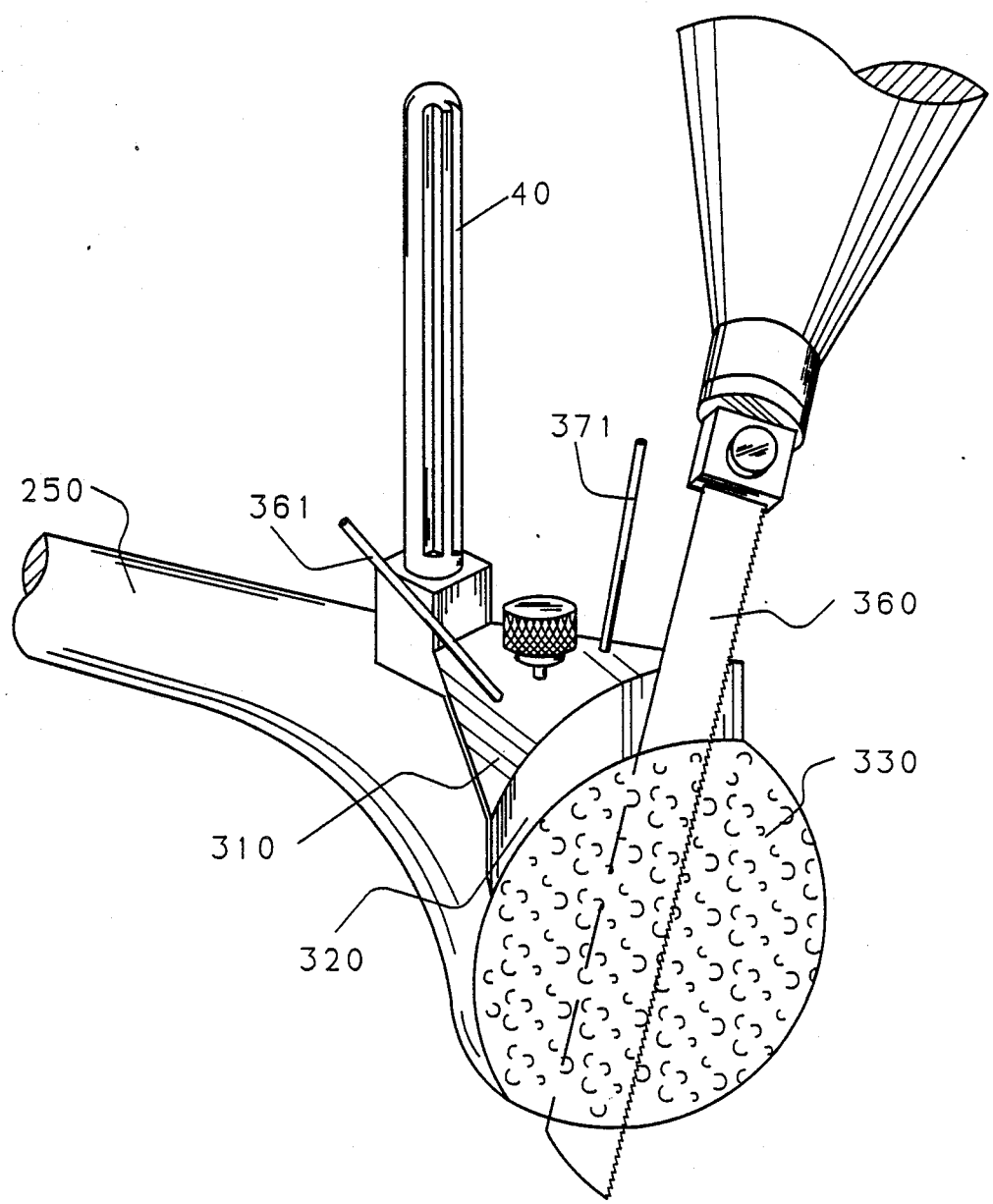
FIG. 9 is a side isometric view of the guide bar and sawguide elements of the device of FIG. 1 showing their typical positioning on the proximal end of a human humerus during the course of the performance of an osteotomy; and, FIG. 10 is an anterior sectional view of the shoulder area of a human being showing an implanted humeral prosthesis, the head of which is articulating with an implanted glenoid prosthesis after implant surgery has been completed.
Figure 10:
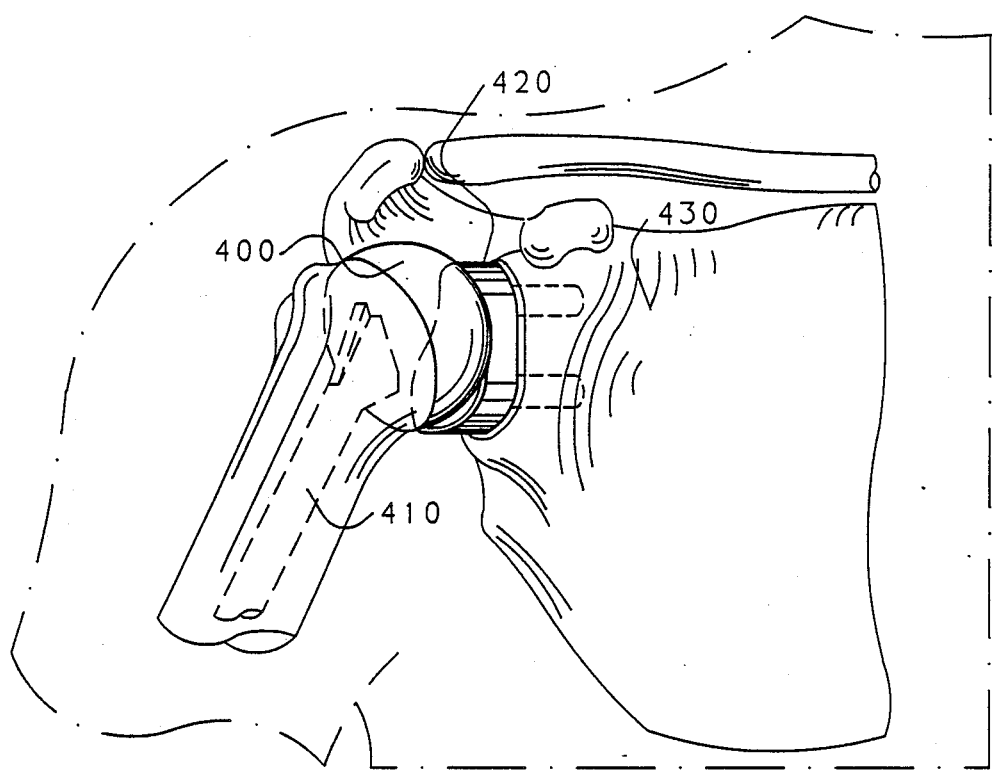

As best shown in FIGS. 6, 7, 8, 9 the guide plate is provided with apertures 360, 370 for receiving stabilizer pins 361, 371. The axes of the apertures 360, 370 are disposed at an angle, i.e. other than parallel, to each other such that when pins 361, 371 are inserted therethrough, the pins 361, 371 penetrate into the proximal end 330 of the humerus 250 as shown in FIG. 7 with their axes being disposed at an angle relative to each other thus serving to eliminate or minimize the possibility that the guide plate 310 might move from its selected positioning on the humeral proximal end 330 during the course of the device's 10 being utilized in the performance of an osteotomy. As shown in FIG. 9 after the guide plate 310 and its associated surface 320 have been locked in a selected position and pins 361, 371 have been inserted into the proximal end 330 of the humerus 250, the surgeon may employ the guide surface 320 as a guide against which a saw blade 360 may be manually urged during the course of cutting the proximal end of the humerus 250.

As shown in FIGS. 1, 2, 5, 6, 7 the sawguide assembly 20 may include a stylus 380 for measuring the size of the proximal end 330, i.e. the humeral head, of the humerus to be cut off. In the embodiment shown in FIGS. 1, 2, 6, 7 the stylus 380 comprises a measuring arm 381 having a measuring surface 383 facing the end surface 320. The measuring arm 381 is disposed on the anterior or upper surface of the guide plate 310 and is secured thereon by a knob 382 and screw 384. The knob 382 is connected to the upper end of the screw 384 which is screwably engaged with a complementary threaded aperture provided in guide plate 310. When the knob 382 is turned in an appropriate direction, the screw 384 draws the knob 382 toward the anterior or upper surface of measuring arm 381, and upon sufficient turning of the knob 382, an undersurface 386 of the knob engages the top surface of arm 381 and frictionally locks measuring arm 381 in a fixed position relative to guide plate 110 and surface 320 such as shown in FIGS. 1, 2, 5, 6, 7. As best shown in FIG. 6 measuring arm 381 includes an axial slot 385 for slidably receiving screw 384. As can be seen from FIGS. 6, 7 measuring surface 383 may be extended away from surface 320 as far as slot 385 may be slid along screw 384. Arm 381 is thus adjustably extendable relative to plate 310 by virtue of screw 384 being slidable through slot 385 and arm 381 is further lockable along the length of slot 385 by virtue of the undersurface 386 of knob 382 being frictionally and lockably engageable on the top surface of arm 381 surrounding slot 385.

In operation, the stylus 380 is provided for allowing the user to measure the size of the portion of the proximal end 330 to be cut off by extending arm 381 so far along slot 385 as to position surface 383 against the most proximal edge of end 330 of humerus 250. A series of stepped measurement indicators 390 are provided on the top surface of arm 381 which are calibrated to correspond to the distance between surfaces 383 and 320. The user may thus determine the distance between surfaces 383 and 320 by reading the correspondence of a stepped indicator 390 with a reference such as surface 320. Once the user has determined the distance between surfaces 383 and 320 by reading a stepped indicator 390, the proper size of the head element 400, FIG. 10, of a prosthetic humeral implant 410 may be determined and thus the proper sized implant may be readily selected during the course of the osteotomy surgery.

Measurements made by reading the calibrated stepped indicators 390 may also be utilized in determining the necessary and proper size of a glenoid prosthetic implant 420 which may also be implanted in the human scapula 430 during the course of the osteotomy surgery and whose proper size and configuration are to some extent determined by the selected size of the head 400 which articulates therewith.

As shown in FIGS. 2, 8 when cups 200, 201 are snugly engaged with the distal end of the humerus 250, the cross arm 70 and distal end of radial arm 30 are supported above, typically anteriorly of, the humerus 250. Further as shown, when the underside edge 321 of plate 310 is engaged with the end 330 of the humerus and the bar 40 is lockably engaged with screw 51, FIG. 5, the proximal end of radial arm 30 is supported above the humerus 250. When the device is used in connection with a normal human humerus 250, the radial arm 30 is generally disposed along an axis which is approximately parallel to the axis of the humerus, the arm being provided with the rotational 90 and distal to proximal 80 slidable capability for purposes of accomodating variably sized and shaped human humeri.

As best shown in FIGS. 1, 2 the epicondyle arms 140, 150 are mounted in complementary slots 71, 72 which are slanted such that the cross arm 70 is disposed proximally of the condyles 230, 240, i.e. the epicondyle arms 140, 150 slant proximally when the cups 200, 201 are engaged with the condyles 230, 240. Such proximally slanted mounting of arms 140, 150 in cross arm 70 is preferably provided for purposes of allowing the surgeon to have clear access to epicondyle arm 140, 150 and better manipulate the distal end of the device 10 and engage cups 200, 201 onto condyles 230, 240.

As best shown in FIGS. 1, 2 the guide bar 40 is mounted in the aperture provided in joint 50 and the sawguide 20 is connected to the end of bar 40 such that the perpendicular axis of end surface 320 forms a selected angle Z relative to the axis of humerus 250, typically between about 15 and about 35 degrees and most preferably about 24 degrees. In practical application such orientation of end surface 320 relative to the axis of the humerus 250 typically proves useful in performing normal humeral head osteotomies.

In the embodiment shown in FIGS. 1, 2 the axis of the apertur receiving bar 40 is disposed such that the axis of bar 40 is disposed at an angle of about 90 degrees relative to the axis of arm 30. In alternative embodiments the axis of bar 40 may be disposed at angles other than 90 degrees relative to arm 30 as long as the sawguide 20 is connected to the end of bar 40 such that the perpendicular axis of end surface 320 may be disposed at an angle Z of between about 15 and about 35 degrees relative to the axis of the humerus.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A device for guiding an osteotomy to be performed on the proximal end of a human humerus comprising:

a proximal end sawguide for defining an osteotomy saw line proximal end of the humerus;

a distal end means for stably aligning the sawguide on the proximal end of the humerus;

a radial arm connecting the sawguide and the means for aligning;

the radial arm being rotatably connected to the sawguide at a proximal end thereof for rotatable movement of the sawguide for use in connection with a left or right humerus;

the radial arm being slidably mounted at a distal end in the means for aligning for slidable movement of the radial arm in the distal to proximal direction;

the sawguide engaging a selected surface on the proximal end of the humerus and supporting the proximal end of the radial arm above the humerus;

the means for aligning engaging the distal end of the humerus and supporting the distal end of the radial arm above the humerus.

2. The device of claim 1 wherein the means for aligning includes a distal cross arm having a slot therethrough, the distal end of the radial arm being slidably received through the slot such that the radial arm is slidable in the proximal to distal direction, the cross arm including means for frictionally locking the radial arm within the slot at selected distal to proximal positions.

3. The device of claim 2 wherein the distal end of the radial arm includes a radial slot, the means for frictionally locking comprising a screw means having a pin protruding from the end of the screw means into the transverse slot and through the radial slot of the radial arm, the radial arm being rotatable around the pin and lockable with the screw means in selected rotatable positions.

4. The device of claim 1 wherein the means for aligning includes a distal cross arm slidably receiving the radial arm, the radial arm being slidable in the distal to proximal direction.

5. The device of claim 1 wherein the means for aligning includes a pair of opposing epicondyle arm pivotably connected to opposing ends of a distal cross arm, the epicondyle arms including means for receiving and engaging the distal end of the humerus, the epicondyle arms being pivotable toward and away from each other for allowing the means for receiving and engaging to reversibly receive and engage the proximal end of the humerus, the distal cross arm having slot means for slidably receiving the radial arm, the radial arm being slidable in the slot means in the distal to proximal direction.

6. The device of claim 5 wherein the means for aligning further includes a screw means connected to both of the epicondyle arms for pivoting the epicondyle arms toward and away from each other around their pivotable connection to the distal cross arm.

7. The device of claim 5 wherein the means for pivoting the epicondyle arms comprises a cross screw having a left hand screw end screwably connected to one of the epicondyle arms and a right hand screw end screwably connected to the other of the epicondyle arms, the cross screw being turnable in clockwise and counterclockwise directions, the epicondyle arms being pivotable toward each other upon turning of the cross-screw in one of the clockwise or counterclockwise directions and pivotable away from each other upon turning of the cross-screw in the other of the clockwise or counterclockwise directions.

8. The device of claim 7 wherein the means for pivoting the epicondyle arms further comprises follower means pivotably mounted in each of the epicondyle arms, the followers having complementary threaded apertures for screwably receiving the right and left hand screw ends of the cross screw and being pivotably mounted in the epicondyle arms such that when the cross screw is turned the epicondyle arms pivot within the distal cross arm and the followers simultaneously pivot within the epicondyle arms.

9. The device of claim 8 further comprising a stabilizer means for restricting transverse movement of the cross screw relative to the distal cross arm, the stabilizer means having a transverse aperture for rotatably receiving the cross-screw, the cross-screw having a selected length rotatably received within the transverse aperture of the stabilizer means and including stop means for engaging a surface of the stabilizer means and limiting movement of the cross screw relative to the cross arm.

10. The device of claim 1 further comprising a proximal guide bar connecting the proximal end of the radial arm and the sawguide, one end of the guide bar being rotatably disposed within a complementary mounting aperture in the proximal end of the radial arm, the other end of the guide bar being fixedly connected to the sawguide, the sawguide eeing rotatable in the lateral to medial direction by rotation of the guide bar within the mounting aperture.

11. The device of claim 1 further comprising a proximal guide bar fixedly connected at one end to the sawguide and rotatably disposed at another end within a complementary mounting apertur in the proximal end of the radial arm, the radial arm including means for frictionally engaging and locking the guide bar in selected rotational positions within the complementary aperture.

12. The device of claim 11 wherein the guide bar is axiall slidable within the aperture in the proximal end of the radial arm, the means for frictionally engaging and locking being engagable with the bar such that the bar may be frictionally engaged and locked in selected axial positions.

13. The device of claim 11 wherein the guide bar includes a pair of axial grooves for receiving and engaging the means for frictionally engaging, the grooves being disposed at selected positions on the surface of the guide bar such that the sawguide is disposed at preselected rotational positions relative to the radial arm when the means for frictionally engaging is lockably engaged within the grooves.

14. The device of claim 11 wherein the sawguide comprises a guide plate having an end guide surface extending downwardly from the end of the guide plate, the guide surface having an underside edge having a contour complementary to the contour of the proximal end of the humerus for receiving and engaging a selected surface on the proximal end of the humerus, the guide surface defining a saw line when the underside edge is in engagement with the selected surface of the proximal end of the humerus.

15. The device of claim 11 wherein the sawguide comprises a guide plate extending outwardly from the axis of the guide bar, the guide plate having a proximal end guide surface for defining a saw line on the proximal end of the humerus, the underside edge of the guide surface having a contour complementary to the contour of the head of the humerus for receiving and engaging a selected surface on the head of the humerus.

16. The device of claim 14 wherein the guide plate includes at least two apertures for receiving a pair of stabilizer pins therethrough, the axes of the aperture being disposed at an angle of greater than zero degrees relative to each other.

17. The device of claim 14 further comprising a stylus disposed on the anterior surface of the guide plate for measuring the size of the proximal end of the humerus.

18. The device of claim 17 wherein the stylus comprises a measuring arm slidable along the anterior surface of the guide plate in the distal to proximal direction, the measuring arm having a slot slidably receiving a screw means screwably engaged within a complementary threaded aperture in the guide plate, and frictionally engageable with the anterior surface of the measuring arm along the length of the slot, the measuring arm having a measuring surface extending proximally beyond and facing the end guide surface for engaging the proximal tip of the humerus, the measuring arm being slidable in the distal to proximal direction such that the measuring surface is slidably movable into engagement with the proximal tip of the humerus and lockable in such position by frictionally lockable engagement of the screw means along the length of the slot.

19. A device for guiding an osteotomy to be performed on the proximal end of a humerus comprising:

a proximal sawguide alignable on a selected surface of the proximal end of the humerus for defining a saw line theron;

a radial arm connecting the sawguide to a distal means for stably aligning the sawguide, the distal alignment means comprising a pair of opposing lateral and medial epicondyle arms pivotably engageable with the lateral and medial sides of the distal end of the humerus, the epicondyle arms being pivotably mounted in a distal cross arm, the distal end of the radial arm being slidably mounted in the cross arm for distal to proximal slidable movement therein;

the proximal end of the radial arm being rotatably connected to the sawguide through a proximal guide bar;

the radial arm being supported above the humerus by the proximal guide bar and the epicondyle arms.

20. The device of claim 19 wherein the sawguide includes a guide plate having an undersurface having a contour complementary to the contour of the proximal end of the humerus for receipt and engagement thereof.

21. The device of claim 19 wherein the epicondyle arms include cup means disposed on the ends of the arms, the cup means having apertures being snugly engageable with lateral and medial condyles on the distal end of the humerus upon pivoting of the arms toward each other, the device further including screw means connected to the arms for simultaneously pivoting the arms toward or away from each other.

* * * * *